US005661182A

United States Patent [19]
Abraham et al.

[11] Patent Number: 5,661,182
[45] Date of Patent: Aug. 26, 1997

[54] METHOD FOR LOWERING OXYGEN AFFINITY OF HEMOGLOBIN IN REDCELL SUSPENSIONS, IN WHOLE BLOOD AND IN VIVO

[75] Inventors: Donald J. Abraham, Midlothian, Va.; Claude Poyart, Paris, France

[73] Assignee: Virginia Commonwealth University, Richmond, Va.

[21] Appl. No.: 478,108

[22] Filed: Jun. 7, 1995

Related U.S. Application Data

[63] Continuation of Ser. No. 127,587, Sep. 28, 1993, abandoned, which is a continuation-in-part of Ser. No. 101,501, Jul. 30, 1993, Pat. No. 5,432,191, which is a continuation-in-part of Ser. No. 6,246, Jan. 19, 1993, Pat. No. 5,290,803, and a continuation-in-part of Ser. No. 702,947, May 20, 1991, Pat. No. 5,122,539, which is a continuation-in-part of Ser. No. 478,848, Feb. 12, 1990, Pat. No. 5,049,695, and a continuation-in-part of Ser. No. 722,382, Jun. 26, 1991, Pat. No. 5,382,680, which is a continuation of Ser. No. 623,346, Dec. 7, 1990, abandoned.

[51] Int. Cl.[6] .................... A61K 31/245; A61K 31/195; A61K 31/325; C07C 45/00
[52] U.S. Cl. ................. 514/563; 514/421; 514/486; 514/512; 514/513; 514/533; 514/535; 514/538; 514/833; 560/30; 560/31; 560/32; 560/42; 562/451; 568/452; 568/455
[58] Field of Search ...................... 514/421, 533, 514/512, 513, 535, 538, 486, 563, 833

[56] References Cited

U.S. PATENT DOCUMENTS

| | | | |
|---|---|---|---|
| 4,699,926 | 10/1987 | Abraham et al. | 514/563 |
| 4,704,402 | 11/1987 | Abraham et al. | 514/563 |
| 4,751,244 | 6/1988 | Abraham et al. | 514/563 |
| 5,049,695 | 9/1991 | Abraham et al. | 560/27 |
| 5,382,680 | 1/1995 | Abraham et al. | 562/451 |

OTHER PUBLICATIONS

Abraham, Donald J., Kister, Jean, Joshi, Gajanan S., Marden, Michael C., and Poyart, Claude. "Intrinsic Activity at the Molecular Level: E.J. Ariëns' Concept Visualized", *Journal of Molecular Biology* (1955), 248.

Khandelwal, Shiv R., Randad,Ram S., Lin,Peck–Sun, Meng, Hong, Pittman,Roland N., Kontos,Hermes A., Choi,Sung C., Abraham,Donald J., and Schmidt–Ullrich,Rupert. "Enhanced Oxygenation in vivo by allosteric inhibitors of hemoglobin saturation," *American Journal of Physiology* 265 (Heart Circulation Physiology 34) H1450–H153, 1993.

Wei,Enoch P., Randad,Ramnarayan S., Levasseur,Joseph P., Abraham,Donald J., and Kontos,Hermes A. "Effect of local change in $O_2$ saturation of hemoglobin on cerebral vasodilation from hypoxia and hypotension." *American Journal of Physiology* 265 (Heart Circulation Physiology 34) H1439–H143, 1993.

Kellogg,Glen E., Joshi,Gajanan S., and Abraham,Donald J. "New Tools for Modeling and Understanding Hydrophobicity and Hydrophobic Interactions." *Medicinal Chemistry Research* (1992) 1:444–453.

Kellogg,Glen E., Semus,Simon F., Abraham,Donald J. "Hint: A new method of empirical hydrophobic field calculation for CoMFA." *Journal of Computer–Aided Molecular Design*, 5(1992) 545–552.

Perutz,Max F., Fermi,Giulio, Abraham,Donald J., Poyart, Claude, and Bursaux,E. "Hemoglobin as a Receptor of Drugs and Peptides: X–ray Studies of the Stereochemistry of Binding." *Journal of the American Chemical Society* 1986 108:1064.

Abraham,Donald J., Perutz,Max F., and Phillips,Simon E.V. "Physiological and x–ray studies of potential antisickling agents." *Proceedings of the National Academy of Sciences* vol.,80pp. 324–328, 1983.

Randad,Ramnarayan S., Mahran,Mona A., Mehanna,Ahmed S., Abraham,Donald J. "Allosteric Modifiers of Hemoglobin 1. Desirn, Synthesis, Testing, and Structure—Allosteric Activity Relationship of Novel Hemoglubin Oxygen Affinity Decreasing Agents." *Journal of Medicinal Chemistry* vol. 34 pp. 752–757 1991.

Abraham,Donald J., Wireko,Fred C., and Randad,Ramnarayan S. "Allosteric Modifiers of Hemoglobin: 2–[4–[[3, 5–disubstituted anilino) carbonyl]methyl]pheoxy]–2–methylpropionic Acid Derivatives that Lower the Oxygen Affinity of Hemoglobin in Red Cell Suspensions, in Whole Blood, and in Vivo in Rats." *Biochemistry* vol. 31, pp. 9141–9149, 1992.

Wireko,Fred C., Kellogg,Glen E., and Abraham,Donald J. "Allosteric Modifiers of Hemoglobin 2. Crystallographiclly Determined Binding Sites and Hydrophobic Binding/Interaction Analysis of Novel Hemoglobin Oxygen Effectors." *Journal of Medicinal Chemistry* vol. 34, pp.758–767, 1991.

*Primary Examiner*—Porfirio Nazario-Gonzalez
*Attorney, Agent, or Firm*—Whitham, Curtis, Whitham & McGinn

[57] ABSTRACT

Drug compounds are used as allosteric modifiers of hemoglobin present in red blood cells. The compounds bind to only a single pair of symmetry related sites in the central water cavity of hemoglobin at the Lys $99\alpha$, Arg $141\alpha$, and Asn 108 β residues. When one of the drug compounds is bound to hemoglobin, it will join three separate sub-units of the hemoglobin molecule and stabilize the hemoglobin in a lower oxygen affinity state. Because the compounds used in this method are either not bound by serum albumin or only interact to small degrees with serum albumin, the compounds are active in whole blood and in vivo. The process of allosterically modifying hemoglobin towards a low oxygen affinity state in whole blood and in vivo could be used in a wide variety of applications including in treatments for ischemia, heart disease, wound healing, Alzheimer's, depression, schizophrenia, adult respiratory distress syndrome (ARDS), etc., in extending the shelf-life of blood or restoring the oxygen carrying capacity of out-dated blood, and as sensitizers for x-ray irradiation in cancer therapy, as well as in many other applications.

1 Claim, 6 Drawing Sheets

CFA, R=4-CL

BZF, R=4-CL

L 3,5,   R=3,5-CL
L 3,4,5, R=3,4,5-CL

RSR-4,  R=3,5-CL
RSR-13, R=3,5-Me

MM25,  R=4-CL

METHOD FOR LOWERING OXYGEN AFFINITY OF HEMOGLOBIN IN REDCELL SUSPENSIONS, IN WHOLE BLOOD AND IN VIVO

CROSS-REFERENCE TO RELATED APPLICATIONS

This patent application is a continuation application of application Ser. No. 08/127,587 filed on Sep. 28, 1993 abn. Application Ser. No. 08/127,587 was a continuation-in-part (CIP) application of the patent application having Ser. No. 08/101,501 which was filed Jul. 30, 1993, now allowed as U.S. Pat. No. 5,432,191 which is a CIP application of the U.S. patent application entitled "USING ALLOSTERIC HEMOGLOBIN MODIFIERS TO DECREASE OXYGEN AFFINITY IN BLOOD" filed Jan. 19, 1993, having Ser. No. 08/006,246, filed Jan. 19, 1993 and which issued as U.S. Pat. No. 5,290,803. U.S. Pat. No. 5,290,803 was a CIP of the patent application having Ser. No. 07/702,947, which was filed May. 20, 1991, now U.S. Pat. No. 5,122,539 which was itself a CIP of the patent application having Ser. No. 07/478,848, which was filed Feb. 12, 1990, now U.S. Pat. No. 5,049,695. The subject matter of this application is also a continuation-in-part of the U.S. patent application entitled "ALLOSTERIC HEMOGLOBIN MODIFIER COMPOUNDS" having Ser. No. 07/722,382 which was filed Jun. 26, 1991, now U.S. Pat. No. 5,382,680 and which itself is a continuation of the U.S. patent application having Ser. No. 07/623,346 which was filed Dec. 7, 1990 now abandoned. The text of all of the above-identified patents and patent applications is herein incorporated by reference.

BACKGROUND OF THE INVENTION

1. Field of the Invention

The invention is related to drug compounds or compositions,which are useful as allosteric modifiers of hemoglobin and, more particularly, the invention is directed to the use of certain drug compounds or drug compositions that are effective in allosterically modifying hemoglobin towards a low oxygen affinity state in red blood cell suspensions, in whole blood, and in vivo, despite the presence of normal concentrations of serum albumin.

2. Description of the Prior Art

Several years ago, it was discovered that the antilipidemic drug clofibric acid lowered the oxygen affinity of hemoglobin solutions (Abraham et al., *J. Med. Chem.* 25, 1015 (1982), and Abraham et al., *Proc. Natl. Acad. Sci. USA* 80, 324 (1983)). Bezafibrate, another antilipidemic drug, was later found to be much more effective in lowering the oxygen affinity of hemoglobin solutions and suspensions of fresh, intact red cells (Perutz et al., *Lancet*, 881, Oct. 15, 1983). Subsequently, X-ray crystallographic studies have demonstrated that clofibric acid and bezafibrate bind to the same sites in the central water cavity of deoxyhemoglobin, and that one bezafibrate molecule will span the sites occupied by two clofibric acid molecules. Bezafibrate and clofibric acid act by stabilizing the deoxy structure of hemoglobin, shifting the allosteric equilibrium toward the low affinity deoxy form. Bezafibrate and clofibric acid do not bind in any specific manner to either oxy- or carbonmonoxyhemoglobin.

In later investigations, a series of urea derivatives [2-[4-[[(arylamino)carbonyl]amino]phenoxy]-2-methylpropionic acids] was discovered that has greater allosteric potency than bezafibrate at stabilizing the deoxy structure of hemoglobin and shifting the allosteric equilibrium toward the low oxygen affinity form (Lalezari, *Proc. Natl. Acad. Sci. USA* 85, 6117 (1988)).

Drugs which can allosterically modify hemoglobin toward a lower oxygen affinity state hold potential for many clinical applications, such as for the treatment of ischemia, shock, and polycythemia, and as radiosensitizing agents. Unfortunately, the effects of bezafibrate and the urea derivatives discussed above have been found to be significantly inhibited by serum albumin, the major protein in blood serum (Lalezari et al., *Biochemistry*, 29, 1515 (1990)). Therefore, the clinical usefulness of these drugs is seriously undermined because in whole blood and in the body, the drugs would be bound by serum albumin instead of reaching the red cells, crossing the red cell membrane, and interacting with hemoglobin protein molecule to produce the desired effect.

SUMMARY OF THE INVENTION

It is an object of this invention to provide a method for allosterically modifying hemoglobin in whole blood and in vivo which utilizes drug compounds or compositions that bind to specific sites on the sub-units of the hemoglobin molecule to stabilize hemoglobin in its low oxygen affinity state, but which do not lose their allosteric modifying effectiveness in the presence of normal concentrations of serum albumin found in blood.

According to the invention, it has been discovered that certain drug compounds are active as allosteric modifiers of hemoglobin, even in the presence of serum albumin. Therefore, these compounds maintain their activity when added to red blood cell suspensions containing serum albumin, when added to whole blood, and when provided in vivo to a patient. The process of allosterically modifying hemoglobin towards a low oxygen affinity state in whole blood and in vivo could be used in a wide variety of applications including in treatments for ischemia, heart disease, wound healing, Alzheimer's, depression, schizophrenia, adult respiratory distress syndrome (ARDS), etc., in extending the shelf-life of blood or restoring the oxygen carrying capacity of out-dated blood, and as sensitizers for x-ray irradiation in cancer therapy, as well as in many other applications.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1A:
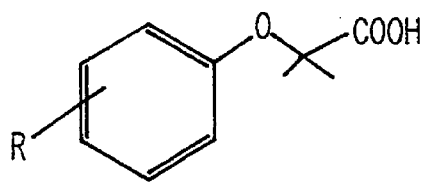
FIGS. 1a–1e are chemical structures of a variety of compounds.
Figure 1B:
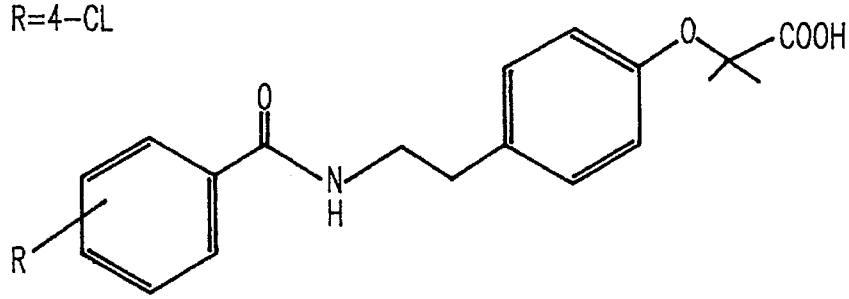
Figure 1C:
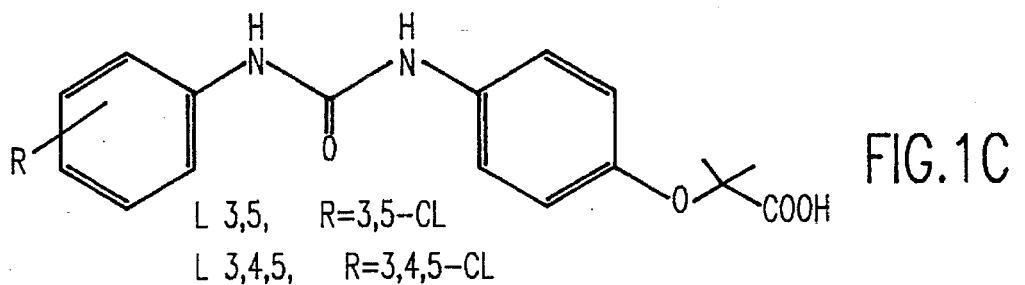
Figure 1D:
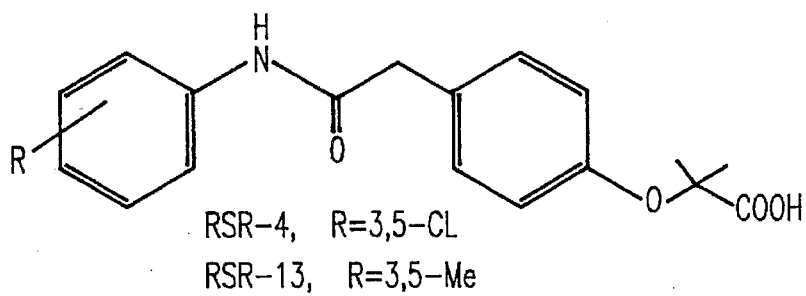
Figure 1E:
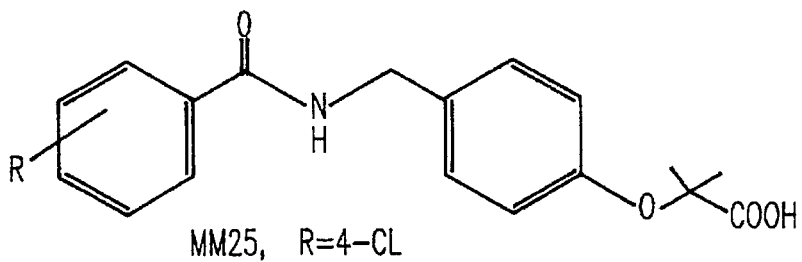

FIGS. 1a–e show the chemical structures of a variety of compounds that have a "right-shifting" allosteric effect on hemoglobin. As discussed above, the clofibric acid compound of FIG. 1a has only a relatively small effect in terms of lowering the oxygen affinity of hemoglobin, while bezafibrate, shown in FIG. 1b, and the urea compounds of Lalezari (L3,5 and L3,4,5), shown in FIG. 1c, have a much stronger allosteric effect. The RSR and MM compounds of FIGS. 1d and 1e, respectively, are representative of a large family of compounds and are discussed in the co-pending patent applications having Ser. No. 08/101,501, Ser. No. 08/006,246, Ser. No. 07/722,382, and Ser. No. 07/623,346, and in U.S. Pat. Nos. 5,122,539 and 5,049,695. The RSR compounds have been found to have a very strong allosteric effect, while the MM series of compounds have been found to have a relatively weaker effect.

This invention is related to the use of allosteric hemoglobin modifier compounds in red blood cell suspensions, in whole blood, and in vivo. Serum albumin, which is the most abundant protein in blood plasma, has been identified as inhibiting the allosteric effects of clofibric acid, bezafibrate, and L3,5/L3,4,5. The precise nature of this inhibition is not fully understood, but appears to be related to these compounds binding to the serum albumin. By contrast, as will be discussed in detail below, the RSR compounds have been found to be relatively unaffected by the presence of serum albumin. Allosteric hemoglobin modifier compounds that are not adversely effected by serum albumin represent particularly good candidates for drug applications, since the performance of the drug will not be frustrated by the presence of serum albumin present in a patient's blood.

Exemplary allosteric hemoglobin modifier compounds include compounds having the structural formula:

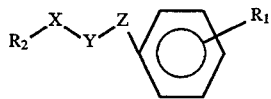

where $R_2$ is a substituted or unsubstituted aromatic compound, or a substituted or unsubstituted alkyl ring compound, or a heterocyclic compound, or a substituted or unsubstituted phthalimide compound that incorporates X and Y where X is a carbonyl, Y is a nitrogen and $R_2$ completes the phthalimide compound by being bonded to both X and Y, and where X, Y, and Z are $CH_2$, NH, S, $SO_2$, CO, O or N with the caveat that the X, Y, and Z moieties are each different from one another, and where $R_2$ has the formula:

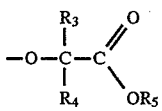

where $R_1$ can be connected to any position on the phenyl ring, and $R_3$ and $R_4$ are hydrogen, halogen, methyl, ethyl, propyl, isopropyl, neopentyl, butyl, or substituted or unsubstituted aryl groups and these moieties may be the same or different, or alkyl moieties as part of an aliphatic ring connecting $R_3$ and $R_4$, and $R_5$ is a hydrogen, halogen, $C_{1-3}$ loweralkyl, or a salt cation.

However, it should be understood that other allosteric hemoglobin modifier compounds that bind to the same binding site on hemoglobin as the RSR-4 and RSR-13 compounds (as described below) and which are not affected by serum albumin might also be used. These compounds could include compounds with two or four membered bridges between the phenyl constituents of the RSR compounds instead of the "X-Y-Z" three membered bridge, compounds where the bridge members are substituted with aromatic, aliphatic, and cycloaliphatic species, as well as compounds with different substitutions on the phenyl rings.

Below are presented detailed studies concerning the oxygen-releasing properties of RSR-4 and RSR-13. The properties of these compounds are compared to L3,5 and L3,4,5 in normal adult hemoglobin (HbA) and bovine hemoglobin. The oxygen dissociation curves at physiological concentrations of serum albumin with hemoglobin solutions or whole blood were carefully evaluated, and efforts were made to determine the membrane transport mechanisms for these molecules. The positive effect of the allosteric effectors RSR-4 and/or RSR-13 on hemoglobin (Hb) with outdated blood and their marked activity in vivo demonstrate their potential clinical usefulness.

Materials and Methods

Human blood was collected on heparin from healthy nonsmoking donors. Bovine blood was provided by Pr Delpech, INA (Paris-Grignon). Red blood cells were washed three times in isotonic buffer, kept at 4° C., and used within 24 h after sampling. Hemoglobin Yakima, a high-oxygen-affinity variant [$\alpha_2\beta_299$ (G1) Asp>>His], was obtained from a known heterozygous carrier. Fresh Yakima red cells were processed in the same way as described above.

L3,5 and L3,4,5 were provided by Dr. Lalezari (Montefiore Hospital, New York); RSR-4 [2-[4-[[(3,5-dichloroanilino)carbonyl]methyl]phenoxy]-2-methylpropionic acid] and RSR13 [2-4-[[(3,5-dimethylanilino)carbonyl]methyl]phenoxy]-2-methylpropionic acid] have been synthesized following the procedure described in Randad et al. (J. Med. Chem. 34,752 (1991)). Human serum albumin (HSA), bovine serum albumin (BSA) and 4,4'diisothiocyanatostilbene-2,2'-disulfonate (DIDS) were purchased from Sigma (St. Louis, Mo.). Due to their low solubility in aqueous buffer, 10 mM stock solutions of the compounds were prepared in a slight exccess of sodium bicarbonate and back-titrated to pH 7.4. For example, RSR-4 or RSR-13 was dissolved at 60° C. in a 140 mM NaCl and 50 mM bis-Tris buffer at room temperature upon progressive addition of $NaHCO_3$ to obtain 10 mM stock solutions. The pH was carefully adjusted to 7.4 after complete solubilization and before use of the solutions. Fresh solutions were prepared each week. Stock solutions of DIDS (1 mM) were prepared, in the dark, on the day of the experiments in a pH 7.4 buffer. Human serum albumin (defatted HSA) and bovine serum albumin (BSA) were prepared freshly as 1 mM stock solutions, pH 7.4. Equilibrium Measurements. The allosteric modulation of the effectors on freshly prepared solutions of hemoglobin or red cell suspensions was measured by the change in $p_{50}$, the partial pressure of oxygen for half-saturation. Oxygen equilibrium curves (OEC) were carried out with the Hemox analyzer (TCS, Southampton, Pa.) under the following conditions: pH 7.4, 140 mM NaCl and 50 mM bis-Tris buffer at 37° C. In all experiments, the concentration of hemoglobin in the red cell suspensions was 20–25 µM hemoglobin tetramer ($Hb_4$) as measured by Drabkin's method (cyanomethemoglobin) at the end of each recording. The final concentration of the allosteric effector in the cuvette was 0.5 mM, resulting in an effector/$Hb_4$ ratio of 20 in the absence of albumin. OEC were also made in the same buffer containing 12.5, 25, 50, and 100 µM HSA (for human red cell suspensions) or BSA (for bovine cell suspensions). The serum albumin experiments were carried out with traces of an antifoaming agent. This agent has no deleterious effect on the red cell suspensions. The molar ratio of albumin to tetrameric hemoglobin was varied from 0.5 (at 12.5 µM HSA) to 4 (at 100 µM HSA); in whole blood this ratio is approximately 0.3 (0.7 mM albumin plus plasma proteins/2.25 mM $Hb_4$). Therefore, the concentration of albumin used in the present studies was always larger relative to tetrameric hemoglobin than that found in whole blood.

Equilibrium oxygen binding curves were also recorded for red cell suspensions (10% hematocrit) that had been reacted for 30 min in the dark at 37° C. with 20 µM DIDS, a specific inhibitor of the red cell membrane anion channel. Kinetic Experiments. The kinetics of the interaction between the effectors and intracellular hemoglobin were measured in the absence and presence of varying concentrations of HSA. The red cell suspensions were equilibrated under room air ($pO_2$=140 mmHg) at 37° C. in the optical cuvette of the Hemox analyzer, which provides a constant stirring of the suspensions. At time 0, the drug was added to the stirred suspensions, which resulted in a rapid increase in absorbance at 560 nm until a plateau was reached, usually within 10 min. Changes in absorbance were recorded and stored on tape for further analyses.

An increase in absorbance at 560 nm ($\epsilon_{max}$ for deoxy-Hb in the visible spectrum) under room air indicates the formation of partially deoxygenated Hb in the red cells and a decreased oxygen affinity of Hb, provided that the pH is held constant. We found that the change in absorbance at 560 nm ($\Delta A560$) upon addition of the effectors was linearly related to the $P_{50}$ values of these cells:

$$p_{50}(mmHg)=220\Delta A560+27.0 (r=0.994)$$

Figure 4:
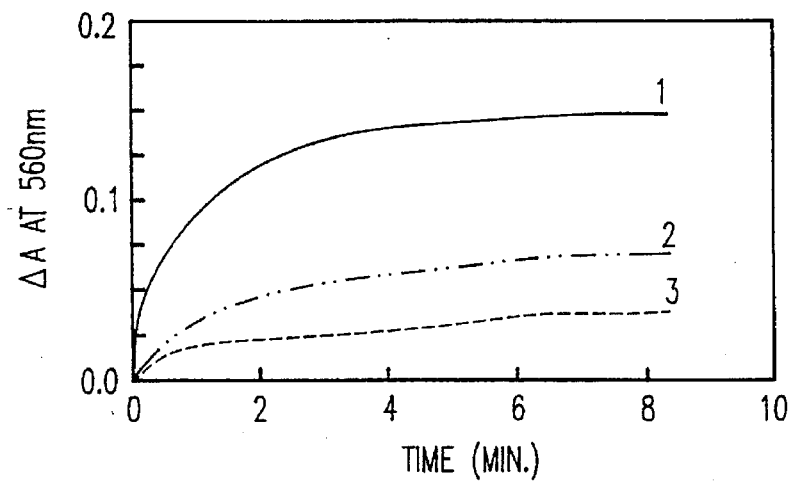
FIG. 4 is a graph showing kinetic recordings of the changes in absorbance ($A_{560}$) versus time after addition of an allosteric hemoglobin modifier compound for increasing concentrations of defatted human serum albumin.

Examples of these kinetic recordings are illustrated in FIG. 4. Two indices were calculated from the experimental values: $\Delta A_{560}$ is the difference in optical density from the base line to the plateau and $t_{1/2}$ is half the time for $\Delta A560$. Any inhibitory effect by albumin was therefore demonstrated by a decrease in either the $p_{50}$ shift or $\Delta A560$ relative to the control values obtained in the absence of albumin.

X-ray Crystallographic Studies. Hemoglobin for the crystal studies was prepared from human blood, and T-state deoxy crystals were obtained from ammonium sulfate solutions. RSR-4 or RSR-13 (2 effectors/I Hb) was dissolved in a slight excess of sodium bicarbonate to facilitate dissolution and was added to a 6 g % solution of deoxy-Hb in the glove box. A 1 g % Hb RSR-4 or RSR-13 solution was added to each crystallization tube. Crystals grew in approximately 1 week. X-ray data were collected with Friedel pairs using ω scans on a Rigaku AFC5R diffractometer equipped with a rotating anode and a 60-cm long evacuated beam tunnel. The crystals with allosteric effectors were isomorphous with native deoxy-Hb: RSR-4, 63.2, 83.7, and 53.8 Å, 99.4°; RSR-13, 63.2, 83.6, and 53.7 Å, 99.5°. Data collection (RSR-4 to 2.4-Å and RSR-13 to 2.8-Å resolution) was controlled by TEXAN software from Molecular Structure Corp. (The Woodlands, Tex.). There was little radiation damage to crystals, and new crystals were mounted when standard reference reflection intensities fell by 10%. All data were corrected for radiation damage when appropriate. The R-factors for the Friedel pairs and derivatives vs. native were as follows: RSR-4 (2.4 Å), 14.6% and 18.9%, and RSR-13 (2.8 Å), 7.2% and 12.5%, respectively. The difference electron density maps were obtained using the Cambridge computer programs (CCP4). The highest peaks in the difference electron density maps were observed to be at 7–8σ, and difference density maps were contoured at 3σ and above. The allosteric effector molecules were well resolved and easily fit to the difference density.

Outdated Blood Studies. For the outdated blood studies, 40-day-old packed red cells (80% hematocrit) were obtained from the blood bank at the Medical College of Virginia, Richmond, Va. The cells had been stored in Adsol formulation at 1°–4° C., pH 6.84. Fresh red cells obtained from volunteers were used for the control studies in Table III. The fresh red blood cells were centrifuged and washed with saline, pH 6.8. The oxygen dissociation curves were recorded on an Aminco Hem-O-Scan (Travenol Laboratories).

In Vivo Studies. The in vivo effect of RSR-4 and RSR-13 was assessed in conscious rats that received (through a chronic femoral vein catheter) an initial 85.7±3.7 mg/kg dose of RSR-4 or 84.0±4.0 mg/kg dose of RSR-13, followed by 85.7±3.7mg/(kg h) RSR-4 or 84.0±4.0 mg/(kg h) RSR13, respectively, for 2 h. The oxygen dissociation curve was measured before infusion with a Hemox analyzer and, after the 2-h infusion, was manually measured with a tonometer and visible spectroscopy to avoid a dilution step (used with the Hemox analyzer) that would disrupt the equilibrium between the drug and erythrocytes. Tonometry was performed at a constant/$pCO_2$ of 40 mmHg at 37° C. The pH of the blood was 7.443±0.012 (n=5) for the RSR-13 experiment and 7.412±0.098 (n=7) for the RSR-4 experiment. Control rats received an infusion of buffer solution with $NaHCO_3$. A slight molar excess of NaHCO3 was used to better solubilize RSR-4.

Results

Oxygen Equilibrium Studies.

Table 1 presents the oxygen binding measurements for fresh human red blood cells on addition of the effects L3,5, RSR-4, and RSR-13 where the conditions for measurements were as follows: pH 7.4, 140 mM NaCl and 50 mM bis-Tris buffer, at 37° C. In Table 1, $p_{50}$ is the partial pressure of oxygen for half-oxygen saturation (mean of at least two measurements); HSA is human serum albumin (defatted); the hemoglobin concentration was 20–25 µM on a tetramer basis; the effector to tetrameric Hb molar ratio was 20 in the absence of HSA; the HSA/$Hb_4$ molar ratio was varied from 0.5 to 4; $\Delta A_{560}$ is the maximum absorbance change at 560 nm under room air on addition of the effector; and $t_{1/2}$ is the time(s) for half-$\Delta A_{560}$. For the DIDS measurements, red cells were incubated for 30 min. at 37° C. at pH 7.4 in the presence of 20 mM DIDS prior to the recording of the oxygen binding curves.

TABLE 1

| Effector (0.5 mM) | HSA (µM) | $P_{50}$ (mm Hg) | $\Delta A_{560}$ | $t_{1/2}(s)$ |
| --- | --- | --- | --- | --- |
| none | none | 27 | | |
| L3,5 | none | 60 | 0.181 | 33 |
| | 12.5 | | 0.124 | 92.5 |
| | 50.0 | 32 | 0.058 | 110 |
| | 100.0 | 28 | 0.029 | 115 |
| +DIDS | none | 54 | nd | nd |
| RSR-4 | none | 52.5 | 0.152 | 60 |
| | 12.5 | 48.5 | 0.107 | 92 |
| | 50.0 | 44.0 | 0.086 | 76 |
| | 100.0 | 36 | 0.042 | 87 |
| +DIDS | none | 49 | nd | nd |
| RSR-13 | none | 37.8 | 0.085 | 139 |
| | 50.0 | 34.0 | 0.082 | 138 |
| | 100.0 | 32.6 | 0.067 | 125 |

Table 1 demonstrates that, in the absence of human serum albumin, RSR-4 and L3,5 are almost equally potent effectors in raising the $p_{50}$ of hemoglobin in fresh human red cells containing normal concentrations of 2,3-diphosphoglycerate. However, the allosteric effect produced by RSR-4 is much less inhibited by 50 or 100 µM albumin than observed with L3,5. While RSR-13 is the weakest in reducing the oxygen affinity of Hb, relative to L3,5 or RSR-4, it is much less affected by serum albumin, and its effect persists even in the presence of 100 1-M HSA.

Figure 2:
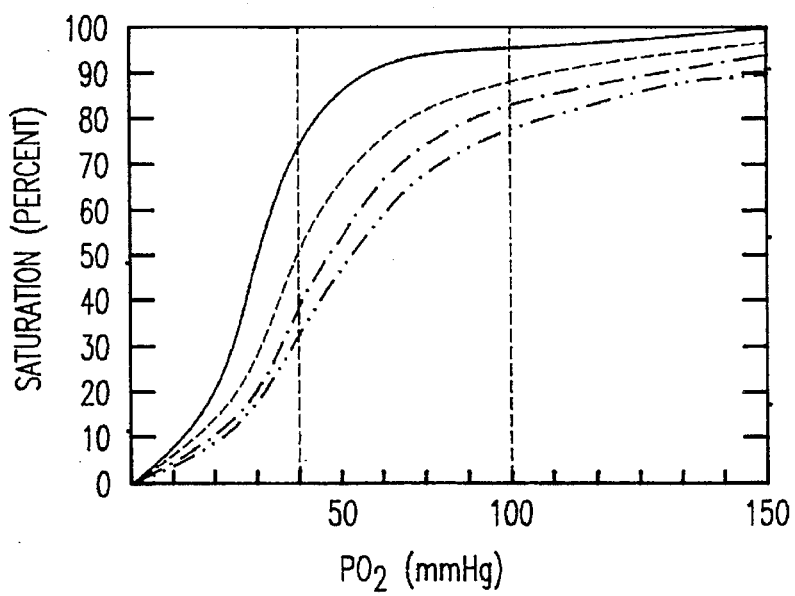
FIG. 2 is a graph showing equilibrium binding curves for human red cell suspensions.

FIG. 2 shows the oxygen equilibrium binding curves for a fresh red blood cell suspension upon addition of RSR-4 With and without HSA. In FIG. 2, curve (1) is the control, curve (2) is the suspension plus 0.5 mM RSR-4, curve (3) is the suspension plus 0.5 mM RSR-4 plus 50 µM HSA, and curve (3) is the suspension plus 0.5 mM RSR-4 plus 100 µM HSA. The concentration ratios of albumin/Hb are above those found in vivo. For example, in curve (3) serum albumin is about six times and in curve (4) about twelve times in excess above the concentration ratio of albumin/Hb found in vivo. The vertical lines indicate the physiological $pO_2$ values in the arterial blood (90 mmHg) and in the mixed venous blood (40 mmHg). The change in oxygen saturation between these two lines allows an estimation of the capability of the red blood cells to deliver oxygen to tissues ($\Delta Y$ (%), as discussed below in conjunction with Table 4).

Figure 3:
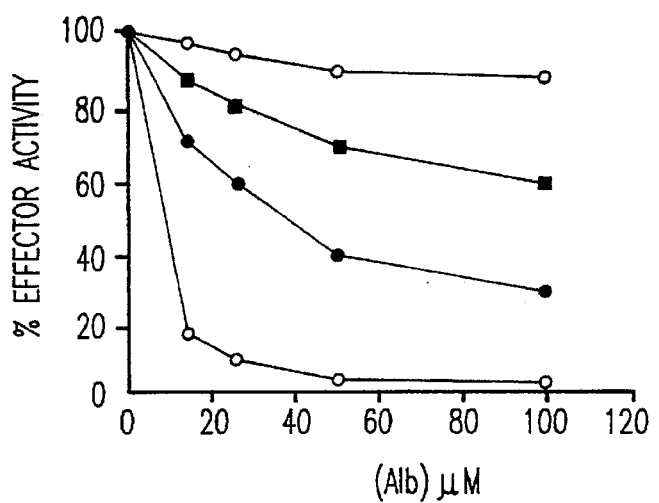
FIG. 3 is a graph showing the percent of allosteric effector activity detected for a variety of compounds in the presence of serum albumin in buffered red cell suspensions.

FIG. 3 summarizes the differences in allosteric effector activity for L3,4,5, L3,5, RSR-4, and RSR-13 in the presence of serum albumin in buffered red cell suspensions. In FIG. 3, the percent of effector activity is shown as open circles for RSR-13, solid squares for RSR-4, solid ciruclcs for L3,5, and open squares for L3,4,5. In the experiment, the effector concentration was 0.5 mM except for L3,4,5 which was 0.25 mM, and hemoglobin concentration was 20–25 µM on a tetramer basis. FIG. 3 shows RSR-13 is by far the least affected by serum albumin inhibition and exhibits greater than 90% allosteric effector activity even in the presence of 50 µM albumin, which is approximately seven times the albumin/Hb ratio present in vivo. RSR-4 effector activity is also greater than L3,5 and L3,4,5 at all serum albumin/Hb ratios studied.

Kinetic Studies on the Transport of Allosteric Effectors across Red Cell Membranes. The results from the kinetic studies are also presented in Table 1 above. In the absence of albumin, $t_{1/2}$ is 33 s for L3,5, 1 min for RSR-4, and over 2 min for RSR-13. The differences in $t_{1/2}$ are probably due to structural differences. For example, FIG. 1 shows the 3,5-dichloro atoms in L3,5 and RSR-4 are substituted by methyl groups in RSR-13. In the presence of albumin, the $\Delta A_{560}$ is decreased and the $t_{1/2}$ values are increased. However, the $t_{1/2}$ values are independent of the concentration of albumin, whereas AA is not. This may indicate that, at a concentration of 12.5 µM , HSA is saturated with the effector. No change in $t_{1/2}$ was observed for RSR-13 upon addition of albumin.

FIG. 4 illustrates a typical example of the kinetic results. In FIG. 4, kinetic recordings were made of the changes in absorbance ($A_{560}$) versus time after addition of 0.5 mM RSR-4 at increasing concentrations of defatted serum albumin for red blood cell suspensions equilibrated under room air. The experimental conditions were pH 7.4, 140 mM NaCl, and 37° C. Curve (1) is a control, curve (2) is the red blood cell suspension with 50 µM HSA, and curve (3) is the red blood cell suspension with 100 µM HSA. It is noted that curves (2) and (3) correspond with (2–4) in FIG. 2.

Table 1 also shows the presence of DIDS, a specific covalently bound inhibitor of the membrane anion channel, does not inhibit the effects of the compounds. This was also true for L3,4,5 (not shown) and indicates that the mechanism by which these compounds penetrate into the red cells is likely to be a diffusion process, probably driven by the affinity of the huge concentration of Hb in the cells.

Bovine Red Cell Studies. Table 2 presents data for oxygen binding measurements for fresh bovine red blood cells and isolated Hb solutions on addition of the effectors L3,5, RSR-4, and RSR-13. The experimental conditions used were the same as described in conjunction with Table 1 for human red blood cells. The oxygen equilibrium curves for Hb solutions were made at pH 7.2, 100 mM NaCl and 50 mM bis-Tris buffer at 25° C. Catalase (20 µg/mL) and 50 µM EDTA were added to oppose oxidation of the hemes. The concentration of the effectors was 0.5 mM in all conditions. In Table 2, BSA is bovine serum albumin and $P_{50}$ (mmHg) is the $pO_2$ for 50% saturation.

TABLE 2

| Effector | RBC ($p_{50}$) | HbA($p_{50}$) | Hb bovine($p_{50}$) |
| --- | --- | --- | --- |
| control | 27 | 5 | 14.5 |
| L3,5 | 35 | 47 | 37 |
| RSR-13 | 31 | nd | nd |
| RSR-4 | 54 | 35.5 | 59 |
| RSR-4 + 50 µM BSA | 45 | nd | nd |

Table 2 compares the $p_{50}$ shifts induced by the effectors for bovine red cell suspensions and isolated bovine Hb solutions to those observed for human Hb. It is known that bovine red cells, which do not contain DPG, exhibit a $p_{50}$ value similar to that of fresh human red cells. By contrast, the $p_{50}$ value of isolated bovine Hb is about three times higher than human HbA. It has also been demonstrated that bovine Hb does not bind exogenous organophosphates in the presence of 100 mM chloride, but does bind these effectors in the absence of chloride. The results given in Table 2 show that the three effectors, L3,5, RSR-4, and RSR-13, bind to bovine Hb in red cells. Interestingly, while L3,5 and RSR-13 induce a small $p_{50}$ shift (30% and 15%, respectively), the effect of RSR-4 results in the doubling of the control $p_{50}$ and persists even in the presence of 50 µM BSA.

Differences in the $p_{50}$ shifts between human and bovine red cells were also observed. Specifically, the order of potency in lowering the oxygen affinity was L3,5≈RSR-4>RSR-13 in human (Table 1) and RSR-4>>L3,5>RSR-13 in bovine (Table 2). Table 2 shows a similar potency was observed in Hb solution studies with the RSR-4 effect being significantly larger than that of L3,5.

Since these effectors bind in the Hb central water cavity at sites which have also been implicated for chloride binding, the role of increasing chloride concentration (0–400 mM) with bovine and human Hb solutions in the presence of RSR-4 and L3,5 was investigated. Surprisingly, the $p_{50}$ shifts induced by the two compounds (0.5 mM) were identical at all chloride concentrations, indicating that RSR-4 and L3,5 antagonize chloride binding in both human and bovine hemoglobin solutions. Conversely, these results demonstrate that the differences in the effects of RSR-4 and L3,5 in the two hemoglobin solutions cannot be ascribed to differences in chloride reactivity.

The reason for the apparent difference in RSR-4 binding to bovine Hb relative to the closely related L3,5 compound requires further investigation. The key residues in human Hb that bind with the allosteric effectors are Lys 99α, Arg 141α, and Asn 108β. These residues are also present in bovine hemoglobin. A stronger interaction by RSR-4 with these same residues or with other sequence differences in bovine Hb must probably account for the increased allosteric effect of RSR-4 vs L3,5 and RSR-13.

Outdated Blood Studies. The capability of RSR-13 to restore the oxygen affinity of stored blood was investigated. The procedure involved measurement of the oxygen equilibrium curves on red cell suspensions, which were stored in Adsol formulations at 4° C., in either the absence (controls) or presence of RSR-13. Table 3 presents the $p_{50}$ (mmHg) and $\Delta Y$ (%) [Y(90%)–Y(40%)] for outdated red blood cell suspensions (forty days) in the presence or absence of RSR-13.

TABLE 3

| origin | effector | $p_{50}$(mm Hg) | $\Delta Y$ (%) |
| --- | --- | --- | --- |
| fresh human RBCs | none | 38 | 38 |
| stored human RBCs | none | 32 | 31 |
| stored human RBCs | RSR-13 (1 mM) | 39 | 37 |
| stored human RBCs | RSR-13 (2 mM) | 45 | 40 |

The oxygen dissociation curves demonstrate that 1 mM RSR-13 is able to restore, to near normal the oxygen transport capabilities ($p_{50}$ and $\Delta Y$) of 40-day-old red blood cells. Untreated samples (controls) were found to be left shifted to 32 mmHg. This increase in the oxygen affinity of stored blood is attributed to the decreased concentration of DPG. However, the oxygen dissociation curves of samples treated with 1 mM RSR-13 showed a $p_{50}$ of 39 mmHg, comparable with the $p_{50}$ of fresh red cells. The oxygen dissociation curves of samples treated with 2 mM RSR-13 were right shifted further ($p_{50}$ of 45 mmHg). Similar concentrations of RSR-13 were added to 50-, 60-, or 70-day old red cells with similar results. The control oxygen dissociation curves of 60- and 70-day old red cells were right shifted compared to the 40-day-old samples, possibly due to a decrease in pH (Bohr effect). Similarly, it was observed that the pH of the RBC solution treated with RSR-13 (4 mM) was higher than that of untreated samples, suggesting a favorable decrease in the rate of glycolytic metabolism (less pyruvic and lactic acid). A similar effect has been observed with another allosteric effector (See, Hyde et al., Lancet 15 (1984)). Addition of RSR-13, to red cells prior to measurements or during storage, also preserved the oxygen delivery capabilities of red cell hemoglobin. There was no indication of hemolysis at the end of these experiments.

In Vivo Estimates for Percent of Oxygen Delivery. Table 4 presents the calculated oxygen delivery index for red blood cell suspensions in the presence or absence of 0.5 mM L3,5 or RSR-4. The experimental conditions for the experiments of Table 4 were the same as those used for Table 1. The oxygen delivery index was calculated from the experimental oxygen binding curves as the difference in hemoglobin oxygen saturation (percent) corresponding to the $pO_2$ in the arterial blood (90 mmHg) and that in the mixed venous blood (40 mMHg). HbA/Yakima red blood cells were obtained from a heterozygous carrier of the high-affinity Hb variant.

TABLE 4

| origin | effector | HSA (μM) | $\Delta Y$ (%) |
| --- | --- | --- | --- |
| human | control | none | 24.5 |
|  | L3,5 | none | 42 |
|  | +HSA | 50 | 30 |
|  |  | 100 | 25 |
| human | RSR-4 | none | 41.5 |
|  | +HSA | 50 | 39 |
|  |  | 100 | 34 |
| human | none | none | 5 |
| HbA/Yakima | RSR-4 | none | 22 |
|  | +HSA | 50 | 19 |

Table 4 contains the calculated amounts of increased oxygen transport [$\Delta Y$ (%)] using L3,5 and RSR-4. Extrapolation to in vivo values can be estimated; however, the Hb concentration in these studies (50 μM) is much lower than that found in whole blood (about 2 mM). The ratio of drug to hemoglobin required in dilute Hb solutions is much greater than that necessary to obtain the same degree of binding at the higher levels of Hb found in vivo. Table 4 also clearly shows that, even in the presence of HSA, RSR-4 greatly improves oxygen delivery (+60% relative to the control value). This would indicate a potential clinical benefit for patients suffering from hypoxic problems.

Studies with Hemoglobin Yakima, a High-Affinity Mutant. Table 4 also shows measurement of oxygen binding to red cells containing 47% of Hb Yakima ($\alpha_2\beta_2$ D99H), a high-oxygen-affinity, non-cooperative Hb variant. Table 4 shows that, by reducing the oxygen affinity of the functional HbA (53%) in these red cells, RSR-4 is able to restore an almost normal oxygen delivery to the RBC from this patient.

Crystal Structures of RSR-4 and RSR-13 Bound to Deoxyhemoglobin and Allosteric Effector Structure-Activity Relationships. The X-ray determined binding sites for L3,5 and RSR-4 have been reported previously (See, Lalezari et al., Biochemistry 29,1515 (1990), and Wireko et al., J. Med. Chem. 34,758 (1991), respectively). Below, the crystal structure binding site of RSR-13 to hemoglobin is compared to RSR-4, L3,5, bezafibrate, and MM-25 (see FIG. 1). RSR-13 has been found to bind in the central water cavity in a conformation identical to that found for RSR-4. The only difference between the two bound structures results from the difference in bond lengths due to the substitution of methyl for chlorine at the 3,5 positions on the terminal aromatic ring.

Figure 5A:
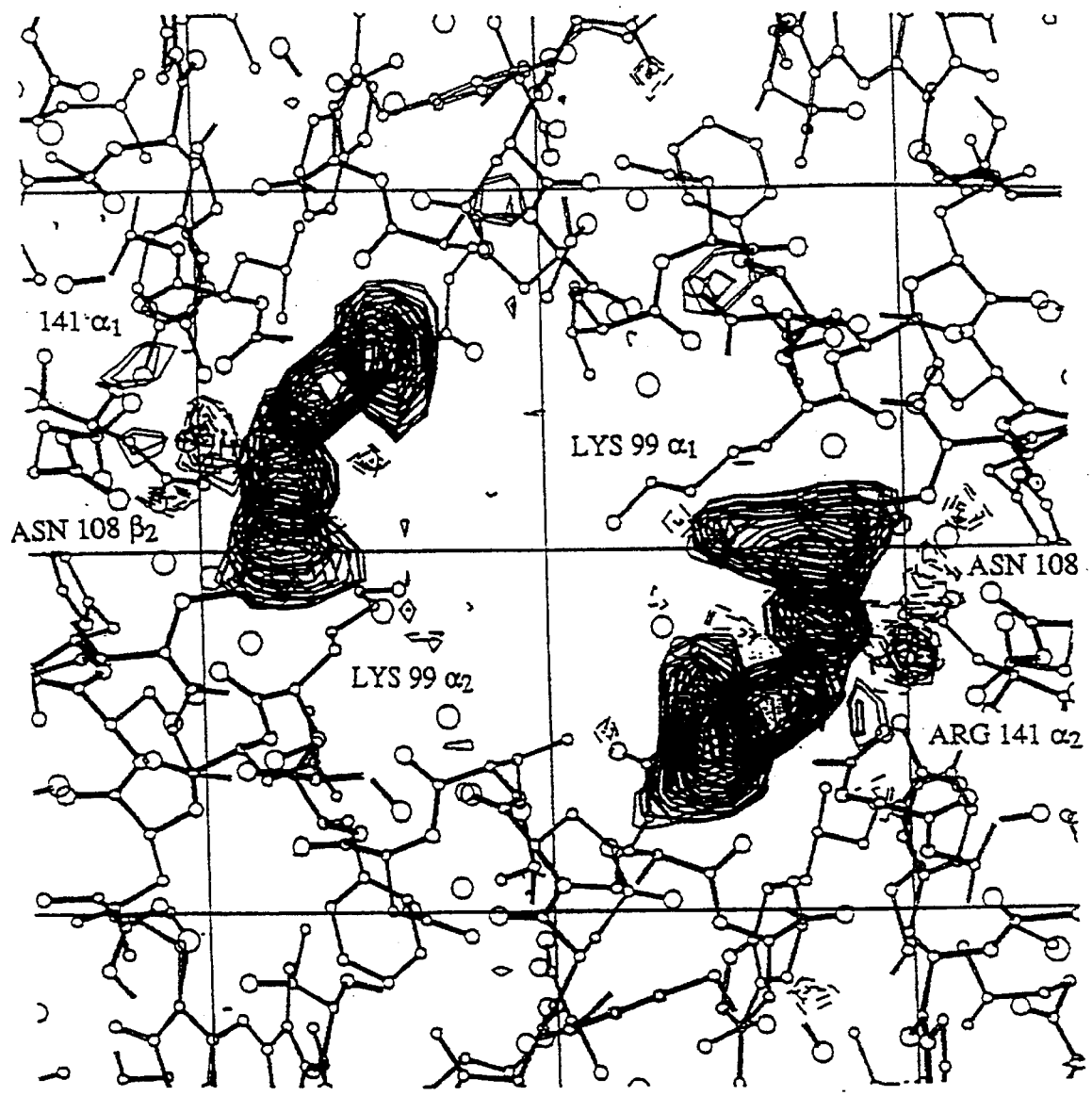
FIGS. 5a and 5b respectively are a view looking down the molecular 2-fold axis that bisects the hemoglobin central water cavity that shows a symmetrical related pair of difference electron density peaks (dark contours) that indicate the position of the allosteric hemoglobin modifier compound, and a stereoview of RSR-13 fit into the difference electron density (a single contour level at $3\sigma$)
Figure 5B:
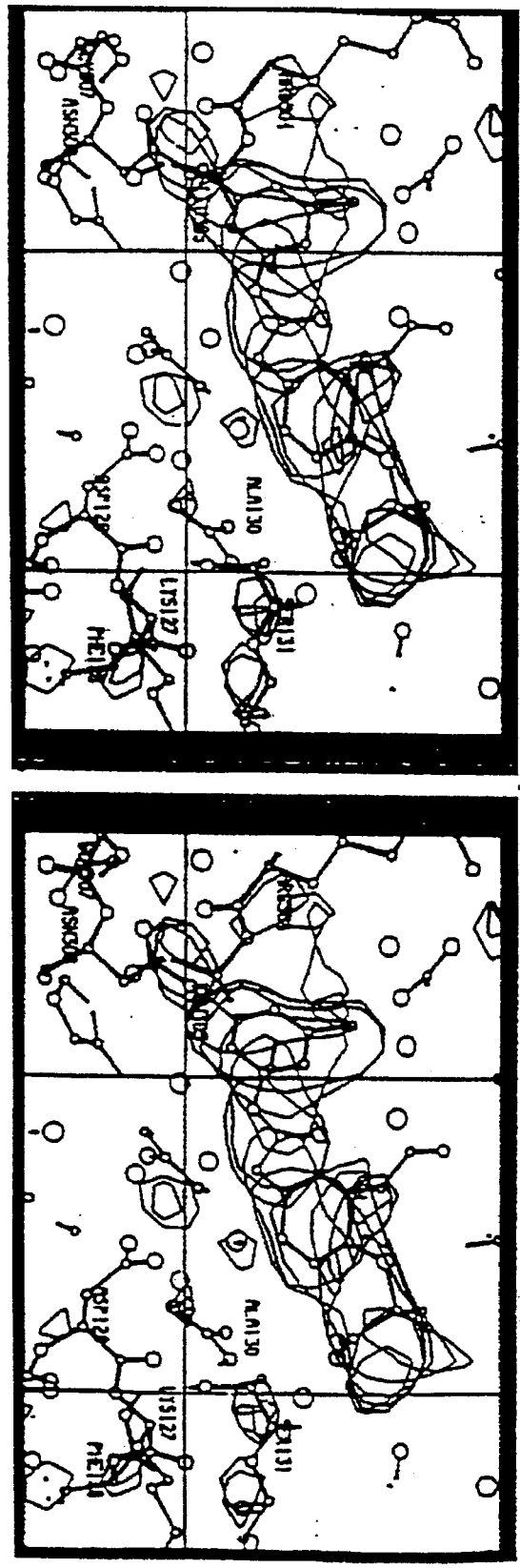

FIG. 5a is a view looking down the molecular 2-fold axis that bisects the central water cavity. A symmetrically related pair of difference electron density peaks (indicated by dark contours) clearly indicates the positions of RSR-13 molecules. Lys 99α, which points into the central water cavity, helps define the primary binding cavity for these effectors. FIG. 5b is a stereoview of RSR-13 fit into the difference electron density (a single contour level at 3σ). It can be seen that RSR-13 difference maps exhibited a symmetry-related pair of densities around the molecular 2-fold axis that bisects the hemoglobin tetramer. The electron density clearly defined the position of the effector at the same locale as that found for bezafibrate. The reason(s) for the differences in allosteric shifts observed for these effectors is (are) not immediately apparent. All of the bis-aromatic effectors shown in FIG. 1 are closely related to bezafibrate, yet MM-25 is somewhat stronger than bezafibrate in its ability to right shift the oxygen equilibrium curve, while the other three molecules are much stronger allosteric effectors with L3,5≈RSR-4>RSR-13 as shown above.

The allosteric effector structure-activity differences can be summarized as follows: (1) The weakest effector, bezafibrate, has a four-atom linkage between the two aromatic rings, while the other effectors have a three-atom bridge. A four-atom bridge may make the effector too long to maximize key interactions. It was previously reported that the halogenated ring of bezafibrate is quite close to the aromatic ring of Phe 36α. (2) The L series has a urea linkage between the aromatic rings, while the RSR and MM series have an amide and methylene bridge between the aromatic rings. (3) The stronger acting RSR series differs from the much weaker MM series by simple reversal of the amide bond. (4) Both weaker acting effectors, MM-25 and bezafibrate, have the amide carbonyl oxygen of the amide linkage next to the halogenated aromatic ring.

A quantitative analysis of protein-allosteric effector interactions was reported previously using a new software package (HINT) developed in our laboratory (See, Wireko et al., *J. Med. Chem.* 34,758 (1991) and Kellogg et al., *Med. Chem. Res.* (1992), both of which are herein incorporated by reference). HINT evaluates and visualizes the degree of hydropathic interactions between a protein and ligand and demonstrated that the major interactions between effectors such as RSR-4 with the protein include the salt bridge between the protonated nitrogen atoms of the Arg 141α guanidinium group with the acid oxygens of the allosteric effector, the interaction of the Lys 99α side-chain ammonium group with the carbonyl oxygen of the effector amide group, and the Ash 108β side-chain NH interaction with the π electrons of the halogenated or methylated aromatic rings of the allosteric effectors.

Figure 6A:
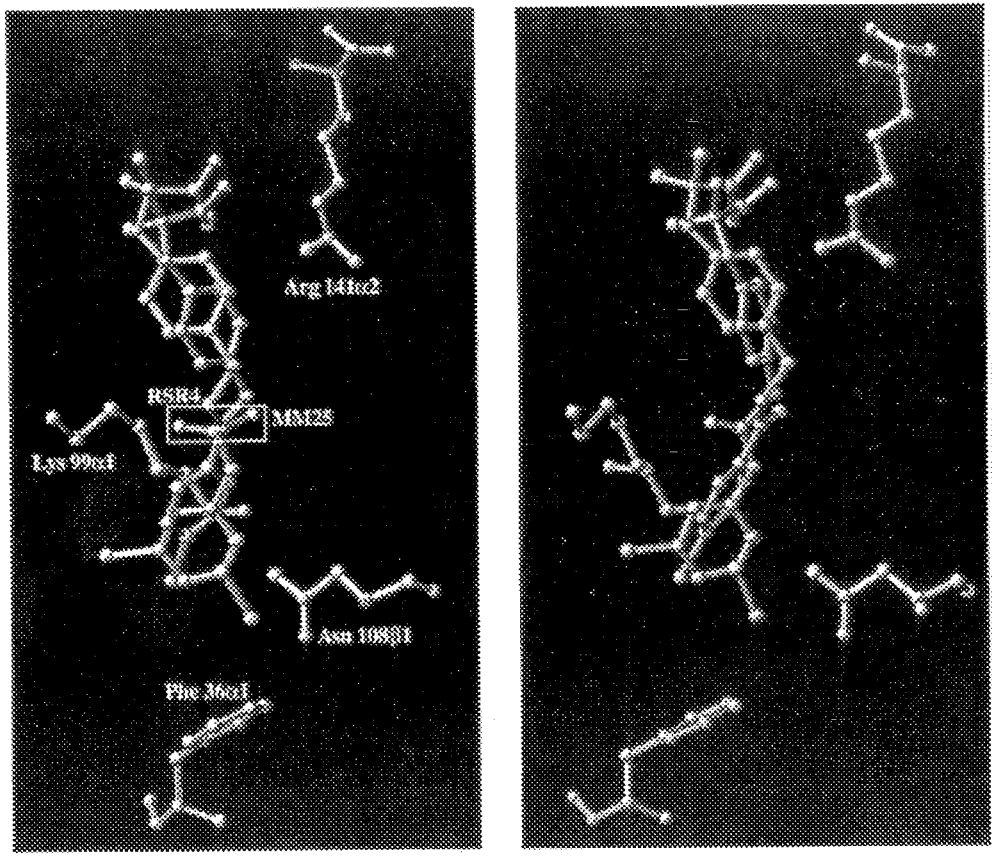
FIGS. 6a and 6b are respectively a stereoview of the overlap of binding of RSR-4 (dark ellipsoids) and MM-25 (clear ellipsoids) at the primary binding site, and a stereoview of the secondary binding site for L3,5 (open circles), L3,4,5 (crosses in circles), and MM-25 (dark circles).

HINT also calculated a significant difference in interaction constants between the RSR and MM series due to the inversion of the amide bond that directs the carbonyl atom of the amide linkage toward the Lys 99α ammonium ion in the RSR (and LR) series but positions the amide oxygen away from the Lys 99α ammonium ion in the MM series. The difference in amide oxygen direction between RSR-4 and MM-25 is shown with the overlapped bound allosteric effectors in FIG. 6a. This single difference in effector amide bond direction appears to be an important component in the degree of allosteric effector activity observed. Solution binding measurements with these and other allosteric effectors show that the differences in binding energies are not correlated with the number of binding sites observed in the crystal and the degree of allosteric shift exhibited by each agent.

Figure 6B:
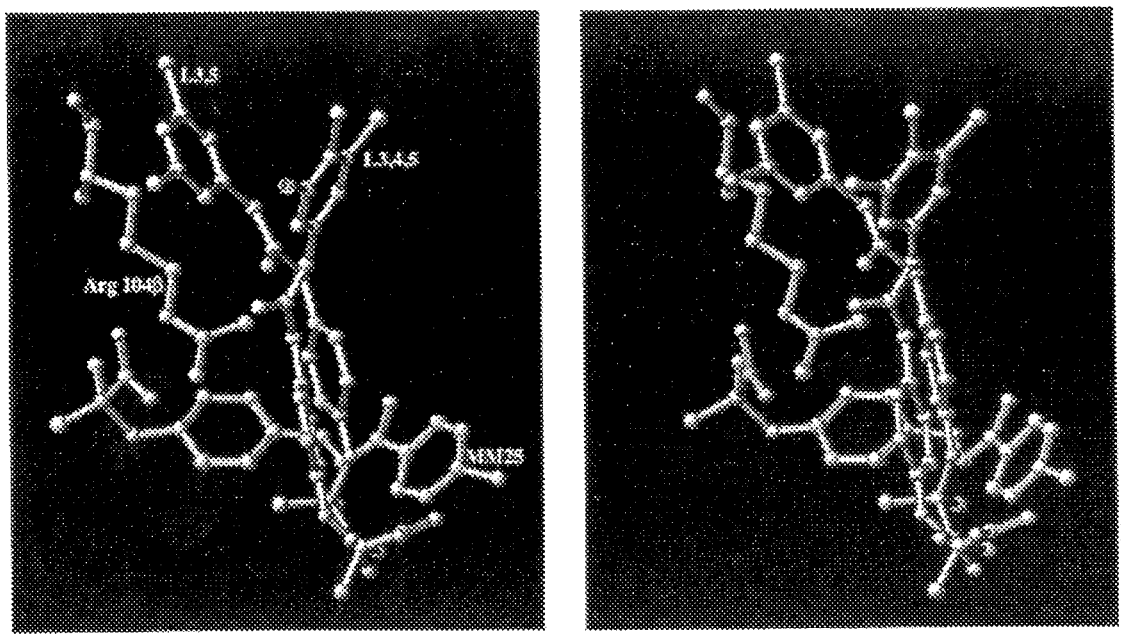

The reason(s) why a few of these effectors, L3,5, L3,4,5, and MM-25 have a second symmetry-related pair of binding sites near Arg 104β, as shown in FIG. 6b, still remain(s) a puzzle. We have determined the crystal binding sites for 15 allosteric effectors with different three-atom arrangements, excluding the L series with the urea linkage. Only four of the effectors exhibited a second binding site. The secondary site is not sterically well defined by the protein and permits a more flexible environment for binding ligands, as can be seen by the three different orientations for L3,5, L3,4,5, and MM25. This secondary site is located in the central water cavity directly below the better defined primarily BZF site. The primary binding site orients the effectors almost vertically along the cavity wall with little variation in binding modes. Lys 99α appears to be a key residue in the formation of a cavity like pocket at the primary binding site by wrapping around the middle of the effectors. There does not appear to be a relationship between the degree of allosteric shift versus the number of sites bound and there is no obvious reason why some effectors have a second binding site and others do not.

In Vivo Studies with the Allosteric Effectors. The above data suggest that RSR-4 and RSR-13 may be promising compounds for lowering whole blood oxygen affinity in vivo. This was confirmed in seven rats in which RSR-4, 85.7±3.7 mg/kg, iv, followed by 85.7±3.7 mg/(kg h) for 2 h, increased $p_{50}$ from an average control value of 36.4±1.6 to 60.7±8.1 mmHg. The Hill coefficient decreased from 2.66±0.13 to 1.74±0.08. In eight control rats the $p_{50}$ decreased from 36.7±1.0 to 33.2±1.4 mmHg. In five rats receiving RSR-13 at 84 mg/kg, followed by 84 mg/(kg h) for 2 h, $p_{50}$ increased from 36.0±2.7 to 61.4±5.8 mmHg. The Hill coefficient decreased from 2.62±0.10 to 1.73±0.08. The animals did not show any sign of distress during infusion of either compound. Significant hemolysis was observed with RSR-4 with rat erythrocytes, but not with RSR-13. The concentration of RSR-4 or RSR-13 in plasma was not measured and cannot be estimated in the absence of data on the volume of distribution and clearance of these drugs. No hemolysis is observed with RSR-4 or RSR-3 with human or bovine red cells under the in vitro conditions described above.

Conclusions

There has been considerable interest in medicine, the military health services, and the pharmaceutical industry in finding methods to increase oxygen delivery in vivo for ischemic insults, stroke, and trauma; to increase blood storage life; to discover radio sensitization agents; and to develop new blood substitutes. In all these instances, the availability of either autologous blood or recombinant Hb solutions is of major interest, provided the oxygen affinity can be decreased to enhance oxygen delivery to the tissues.

The RSR molecules described above are the first strongly acting allosteric effectors that are able to shift the oxygen equilibrium curve (OEC) of red blood cells to a large extent without being grossly affected by serum albumin. In order to exemplify their potential use in vivo, we have calculated the index of oxygen delivery to the tissues, assuming normal arterial and mixed venous blood $pO_2$ values. Table 4 shows that, even in the presence of HSA, RSR-4 improves to a large extent the oxygen delivery to tissues (+60% relative to the control values). Since RSR-4 is less inhibited by albumin than the closely related compound L3,5, RSR-4 exhibits a greater effect in increasing oxygen release to tissues. Even though the $p_{50}$ of RSR-13 is less than that produced by the other effectors, it is large enough to show a significant right shift in vivo. In this regard, it is worth noting that allosteric modifiers that produce too great a shift Of the OEC could inhibit oxygen uptake by red blood cells in the lungs and thereby hinder oxygen delivery in vivo at physiological mixed venous $pO_2$ values. Also, because of its lower affinity for serum albumin, RSR-13 may be the preferred allosteric effector for clinical applications.

Another example of the beneficial effect of RSR-4 was demonstrated in studies of oxygen binding curves with red cells containing 47% of Hb Yakima, a high-oxygen-affinity, noncooperative Hb variant. Table 4 shows that addition of RSR-4 to these red cell suspensions results in an almost normal oxygen delivery index. In this case the $p_{50}$ shift is due to the binding of RSR-4 to the fraction of HbA present in the cells, as purified Hb Yakima remains locked in the high-affinity R-state in the presence of L3,4,5, L3,5, RSR-4, or DPG. More direct information was obtained from the in vivo rat studies. These preliminary experiments demonstrated that the $p_{50}$ shifts measured in rat blood upon infusion of RSR-13 were consistent with the in vitro studies.

In the absence of albumin, the $p_{50}$ shifts that arise from the addition of RSR-4 or L3,5 to human RBC suspensions or HbA solutions are comparable. In the presence of albumin, as shown in Table 1, a large difference was observed between the two compounds with a much lower inhibition of RSR-4 by serum albumin than that observed with L3,5, while RSR-13 is practically unaffected by serum albumin (FIG. 3). The reason for this great difference between the serum albumin inhibitory effect (binding) of RSR-4, RSR-13, and L3,5 to serum albumin is puzzling since the major structural differences between the three compounds are small. L3,5 and L3,4,5 contain a urea bridge between the aromatic rings while RSR-4 and RSR-13 have a methylene group substituted for one of the amide nitrogens in the L series. Since the RSR series is less polar than the L series, it appears that small changes in hydrophobicity and/or structure can play a significant role in changing the affinity to ubiquitous binding proteins such as serum albumin.

The similarity in binding at the primary site for RSR-4, RSR-13, L3,5, and all other allosteric effectors illustrates the basic mechanism by which these molecules act. They keep the T-state Hb molecule from shifting to the R-state oxygenated structure by not permitting the central water cavity to narrow. Each symmetry-related effector molecule at the primary site interacts with three different subunits in the central water cavity tying the two halves of the Hb tetramer together. One effector molecule interacts with the $\alpha_1$, $\alpha_2$, and $\beta_1$ residues, and the symmetry related effector interacts with the corresponding symmetry related residues on the $\alpha_2$, $\alpha_1$, and $\beta_2$ subunits. The natural allosteric effector, 2,3-diphospho-glyceric acid, binds in a similar fashion but at the other end of the tetramer, bridging the $\beta$-subunits. Since DPG binds at a different site, it acts in an additive manner when combined with these allosteric effectors.

While the invention has been described in terms of its preferred embodiments, those skilled in the art will recognize that the invention can be practiced with modification within the spirit and scope of the appended claims.

We claim:

1. A method for allosterically modifying hemoglobin towards a low oxygen affinity state in blood, comprising the step of:

providing blood with a sufficient amount of an allosteric effector molecule which
  (i) binds to only one pair of symmetry related sites in the central water cavity of hemoglobin at the Lys 99$\alpha$, Arg 141$\alpha$, and Asn 108 $\beta$ residues, each pair of symmetry related sites having residues on three separate sub-units of said hemoglobin,
  (ii) stabilizes said hemoglobin in a lower oxygen affinity state, and
  (iii) is active in the presence of normal concentrations of serum albumin in said blood, said allosteric effector molecule
    (a) maintains greater than sixty percent of its activity in terms of right shifting the oxygen dissociation curve of hemoglobin for a buffered red cell suspension at pH 7.4, in 140 mM NaCl and 50 mM bis-Tris buffer at 37° C., which contains 20–25 µM hemoglobin on a tetramer basis, 50 µM serum albumin, and 0.5 mM of said allosteric effector molecule, relative to said buffered red cell suspension without 50 µM serum albumin, and
    (b) maintains greater than eighty percent of its activity in terms of a calculated oxygen delivery index for said buffered red cell suspension containing 50 µM serum albumin relative to said buffered red cell suspension without 50 µM serum albumin; and permitting said allosteric effector molecule to penetrate into erythrocytes in said blood and bind to said hemoglobin therein.

* * * * *